United States Patent
Gohda (10) Patent No.: US 11,945,739 B2
(45) Date of Patent: Apr. 2, 2024

(54) TESTING METHOD FOR WASTEWATER TREATMENT FACILITY

(71) Applicant: GOHDA WATER TREATMENT TECHNOLOGY CO., INC., Tokyo (JP)

(72) Inventor: Toshihisa Gohda, Tokyo (JP)

(73) Assignee: GOHDA WATER TREATMENT TECHNOLOGY CO., INC., Tokyo (JP)

(*) Notice: Subject to any disclaimer, the term of this patent is extended or adjusted under 35 U.S.C. 154(b) by 208 days.

(21) Appl. No.: 17/436,292

(22) PCT Filed: Mar. 11, 2019

(86) PCT No.: PCT/JP2019/009727
§ 371 (c)(1),
(2) Date: Sep. 3, 2021

(87) PCT Pub. No.: WO2020/183577
PCT Pub. Date: Sep. 17, 2020

(65) Prior Publication Data
US 2022/0177337 A1    Jun. 9, 2022

(51) Int. Cl.
C02F 3/00 (2023.01)
C02F 3/12 (2023.01)
G01N 33/18 (2006.01)

(52) U.S. Cl.
CPC ............ C02F 3/006 (2013.01); C02F 3/1236 (2013.01); G01N 33/18 (2013.01); *C02F 2203/006* (2013.01)

(58) Field of Classification Search
CPC ........ G01N 15/04; G01N 33/18; C02F 3/006; C02F 3/1236; C02F 2203/006; C02F 2209/11; C02F 1/5209
(Continued)

(56) References Cited

U.S. PATENT DOCUMENTS

| 10,222,309 | B2 * | 3/2019 | Engels | B01D 21/302 |
| 2013/0220922 | A1 * | 8/2013 | Joensuu | B01D 21/01 |
|  |  |  |  | 210/732 |

FOREIGN PATENT DOCUMENTS

| JP | 06-126293 A | 5/1994 |
| JP | 11-090480 A | 4/1999 |

(Continued)

OTHER PUBLICATIONS

Seka Arsenem et al: "Feasibility of a multi-component additive for efficient control of activated sludge filamentous bulking", Water Research, Elsevier, Amsterdam, NL, vol. 35, No. 12, Aug. 1, 2001 (Aug. 1, 2001), pp. 2995-3003, XP027273118, ISSN: 0043-1354 [retrieved on Aug. 1, 2001].

*Primary Examiner* — Claire A Norris
(74) *Attorney, Agent, or Firm* — Daniel J. Chalker; Edwin S. Flores; Chalker Flores, LLP (57) ABSTRACT

The present invention relates to a testing method for testing a state of an aeration tank in a wastewater treatment facility that uses activated sludge. The testing method comprises obtaining a difference between: a sedimentation amount when a given period of time has elapsed after an activated sludge mixed liquid collected from the aeration tank and water having a higher dissolved oxygen concentration than the activated sludge mixed liquid are poured into the same container and mixed together; and a sedimentation amount when a period of time equal to the given period of time has elapsed after the activated sludge mixed liquid collected from the aeration tank and water having a lower dissolved oxygen concentration than the activated sludge mixed liquid are poured into the same container and mixed together.

18 Claims, 1 Drawing Sheet

(58) Field of Classification Search
USPC .............................. 73/61.71, 61.65; 210/614
See application file for complete search history.

(56) References Cited

FOREIGN PATENT DOCUMENTS

| | | |
|---|---|---|
| JP | 11-160305 A | 6/1999 |
| JP | H11-183365 A | 7/1999 |
| JP | 2010271090 A | 12/2010 |

* cited by examiner (a)

TESTING METHOD FOR WASTEWATER TREATMENT FACILITY

CROSS-REFERENCE TO RELATED APPLICATIONS

This application is the National Stage of International Application No. PCT/JP2019/009727, filed on Mar. 11, 2019, the contents of which is incorporated by reference herein.

TECHNICAL FIELD OF THE INVENTION

The present invention relates to a testing method for testing the state of an aeration tank in a wastewater treatment facility that uses activated sludge, a diagnosis method and an operation management method of a wastewater treatment facility using the testing method, and an apparatus configured to implement the testing method.

BACKGROUND OF THE INVENTION

Global environmental problems are receiving attention, and there is an increasing awareness of the importance of water in recent years. Hence, the need for appropriate maintenance of the operation of wastewater treatment facilities is growing. A common flow in a wastewater treatment facility is as follows. First, there is equipment (screen) that separates large garbage in a pretreatment step. Incoming useless SS matters are removed in this step. The subsequent step is a biological treatment, which is the core of purification. In an aeration tank, air required for activated sludge to work is supplied into the wastewater by aeration (or air blast). In the last step, the purified water is separated from microorganisms, and the purified treated water is sterilized and discharged into a river or the like. As is known in the wastewater treatment industry, in the case where microorganisms live in an aqueous solution containing nutrients and oxygen, the microorganisms repeat reproduction through division, and flocs of microorganisms are formed through the lag phase and the log phase. The reason why the flocs of microorganisms are formed is that bacteria in water in the aeration tank include floc-forming bacteria that secrete an intracellular reserve substance as a sticky substance to sustain life in the middle of the log phase and also catch non-floc-forming microorganisms that do not secrete the sticky substance to form an aggregation of flocs. What takes a leading part in decomposition of organic matters in untreated water is the sludge called activated sludge, which is an aggregate of flocs of microorganisms. When nutrients in the wastewater decrease below a certain limit, the floc-forming bacteria take the secreted sticky substance in the cells again as a nutrient source, and the flocs lose aggregability and are broken up. The field of wastewater treatment widely employs a method of absorbing, digesting, and decomposing water pollutants contained in wastewater using flocs of aerobic microorganisms or facultative anaerobic microorganisms utilizing these characteristics of the microorganisms, sedimenting the microorganism flocs after completion of the decomposition, discharging the supernatant liquid as the treated liquid, extracting a portion of precipitated sludge to the outside of the system as excess sludge, and returning the remaining precipitate sludge to the aeration tank, as represented by the activated sludge method. Accordingly, to perform the wastewater treatment by aeration, a method employed as a fundamentally important operation management method includes keeping the activated sludge concentration in the aeration tank at a concentration necessary and sufficient to purify water pollutants and supplying oxygen necessary and sufficient for the activated sludge to be active to the aeration tank under such conditions as not to break the flocs up due to excessive oxygen. To implement this operation management method, sludge volume (SV) meters, dissolved oxygen (DO) meters, mixed liquor suspended solids (MLSS) concentration meters, oxidation reduction potential (ORP) meters, and the like are used.

However, there are extremely many cases where the load on a wastewater treatment facility widely fluctuates due to various causes. There are extremely many cases, and therefore the cases can be said to be a normal condition, where the amount of load on a wastewater treatment device greatly fluctuates, such as the cases of a facility that shuts down on Saturdays, Sundays, and holidays except for wastewater from automated continuous operation plants of large corporations, a facility that shuts down during the night or late at night, a facility that does not completely shut down but receives a greatly reduced wastewater treatment load late at night and on holidays such as Saturdays, Sundays, and national holidays, a facility, such as a facility in a resort, that conversely receives an abruptly increased wastewater treatment load during holidays such as Saturdays, Sundays, and national holidays, and factory equipment in which production items and the quantity of production items greatly fluctuate depending on the day of the week or the season. In addition to the fluctuation of the amount of load, the concentrations of soluble components and refractory suspended solids (SS) in untreated water widely fluctuate, and the degree of difficulty of the treatment of the untreated water often widely fluctuates. In addition to artificial conditions, changes in the natural environment such as changes in the air temperature and water temperature, changes in the activity of the activated sludge due to changes in the water temperature, and mixing of rainwater also affect the operation management state of the wastewater treatment facility. Quite a few wastewater treatment facilities include untreated water tanks or equalization tanks that store untreated water for about a half day to one day to equalize the loads on the aeration tanks, but there are extremely many cases where the fluctuations in untreated water, water pollutant components, temperatures, SS concentrations, and the like are too large to absorb fluctuations in the loads by the untreated water tanks or the equalization tanks, thereby greatly affecting the operation management conditions of the aeration tanks. The types of microorganisms in the aeration tank are changed by the fluctuations in the load on the aeration tank due to the above-described causes. As described above, to remove water pollutants in the wastewater treatment using microorganisms, it is important to keep the activated sludge concentration in the aeration tank at a proper value. However, in the case where the wastewater contains SS other than the activated sludge and the microorganisms, a method for measuring only the activated sludge concentration at a worksite in a simple and easy way has not been globally developed, and the MLSS concentration measured with an MLSS meter is commonly used as a substitution for the value for the activated sludge. However, there is a considerably large amount of wastewater having an extremely high SS concentration in the untreated water in relation to the BOD loading, such as livestock wastewater and human excreta wastewater, which are one of the largest sources of polluted wastewater in Japan, as well as wastewater from factories that process raw materials containing much vegetable fiber, such as adzuki beans. For example, in the case of wastewater mixed with excrement from pig farms, the SS concentration often falls within the range of about 5,000 to 20,000 mg/kg in relation to a BOD concentration of 8,000 to 10,000 mg/kg. In the case where such wastewater is treated, there are many cases where the proportion of SS other than microorganisms contributing to the MLSS concentration exceeds 80%, and the ratio of activated sludge to the MLSS relatively greatly changes even if the change in the SS concentration other than the microorganisms is 10%.

Accordingly, there are many cases where regarding the MLSS concentration as an approximate value of the activated sludge concentration does not lead to a correct operation management method. The DO concentration is often referred to as a standard of the amount of oxygen supplied required for removal of water pollutants in wastewater using microorganisms. However, the optimal value of DO remarkably varies depending on the structure of the wastewater treatment equipment, the components of water pollutants in untreated water, the residence time in the aeration tank, the water temperature, and the types of the microorganisms. The proper DO value is 2.0 mg/kg in some cases and 0.5 mg/kg in other cases. In particular, in an aeration treatment mainly using facultative anaerobes that take a leading part in decomposition of natural organic matters in the natural world in fields such as the forest, wasteland, and agricultural fields, good treated water quality is often secured at an oxygen content of DO of 0.5 mg/kg or less. Even when such an aeration treatment is performed mainly using facultative anaerobes in wastewater treatment equipment open to the atmosphere, it is considered that the ratio between facultative anaerobes and aerobes fluctuates because of aerobes that are mixed as a matter of course, and the optimal value of DO in the aeration tank is not a fixed value. There are increasing instances where operation management of aeration tanks is performed using ORP meters in recent years. The measured value of ORP of the supernatant liquid obtained by leaving a mixed liquid sample in the aeration tank standing to sediment the sludge is often much more useful for determining the management state of the aeration tank than the measured value measured with a DO meter that measures the concentration of remaining oxygen that has not been consumed. As a general trend, the measured value by an ORP meter is +100 my or more with excessive oxygen, and conversely the measured value is −100 my or less with deficient oxygen. However, the measured value may be a negative value even with excessive oxygen, and appropriate determination may be impossible only with measurement by the ORP meter. In the treatment of untreated water containing water pollutants mainly composed of natural organic matters, the pH of the mixed liquid in aeration tanks often gradually decreases along with absorption, digestion, and decomposition of the load from a first aeration tank to a final aeration tank, but the pH of wastewater containing a high concentration of refractory SS may increase in the final aeration tank along with decomposition of SS.

The primary object of a wastewater treatment facility is to restore generated wastewater to the water quality before use or higher quality and discharge the water. A standard of the discharged water quality is stable water within discharged water quality standards established by the administration. Water is important and valuable in the future in view of our existence and economic efficiency. What is most important to stably keep a high treated water quality is to competently determining whether the operation management state of the final aeration tank (the only aeration tank in a continuous treatment device including only one aeration tank, or in the latter half or at the end of the aeration treatment in a batch aeration tank) is such that the oxygen content is proper in relation to the activated sludge content and the load is sufficiently treated, or the oxygen content is excessive while the load is sufficiently treated and the activated sludge floc is bulking and being broken up, or the load is excessive or the oxygen content is lacking in relation to the activated sludge content. Only when the determination can be quickly and correctly performed, correct measures against troubles over operation management can be taken, or troubles can be prevented from occurring by taking measures at an early stage in the case where the operation management state starts to be off a normal condition. In particular, if excessive aeration is continued for a long time due to an error of determination of the operation management state of the aeration tank, the problems are caused that the activated sludge floc is broken up, sedimentation of the sludge in a sedimentation tank becomes difficult, the sludge is mixed with the discharged treated water, and stable operation of the wastewater treatment equipment cannot continue. Hence, in the wastewater treatment industry, the emphasis is on the wastewater treatment facility, particularly the final aeration tank, a method of measuring the DO, MLSS, pH, SV (30 minutes) and the like, controlling the operation of the aeration device according to the measurement results, and adjusting the extraction amount of excess sludge and the sludge return amount is widely employed. However, appropriate determination on the state in the final aeration tank is often impossible using only the measured values of the DO, MLSS, pH, SV (30 minutes), and the like because of the above-described reasons. In the case of a large-scale facility in which dedicated managers experienced in the operation management of wastewater treatment equipment are engaged in management, correct determination can be made by collectively considering not only these measured values but also observation of phenomena that are difficult to express with values, such as the amount of bubbles, color, and turbidity in the aeration tank. However, in the case of a small and medium-sized wastewater treatment facility in which there is no experienced dedicated operation manager and in which a manager of a facility that is a source of wastewater also serves as the operation manager, the manager is busy in the source of wastewater particularly when the load greatly fluctuates, such as the daily starting time of work, and operation management of the wastewater treatment equipment have to be thinly staffed. Accordingly, development of a method that enables quick and correct determination of the situation of operation of the aeration tank using a simple and easy measuring method is desired.

Japanese unexamined Patent Application Publication No. 6-126293 proposes a method of continuously measuring the DO in an untreated water tank and an aeration tank using a DO meter and/or an ORP meter, measuring the BOD or COD of untreated water flowing into the aeration tank and the inflow of the untreated water, determining the amount of load by multiplying and integrating both values, and controlling the oxygen content such that the DO in the final aeration tank reaches a target DO while estimating the DO in the aeration tank on the basis of the estimated load. However, the work is extremely complicated when the method is implemented manually, but automation of the work requires a complex and expensive device. Japanese unexamined Patent Application Publication No. 11-90480 discloses an operation management procedure of an aeration tank by intermittent aeration procedure or control of the rotation rate of an aeration blower on the basis of a DO measured value measured with a DO meter arranged on an oxidation ditch, but application of this procedure using only the DO measured value to aeration tanks in general is not an appropriate operation management method as described above. Japanese unexamined Patent Application Publication No. 11-160305 proposes a testing method including repeating an inspection set including inserting a sample waste liquid into a mixed liquid in an aeration tank and determining changes in DO in the process of aeration (step 1), halting aeration to interrupt the dissolution of oxygen from the outside and measure the decreasing speed of DO (step 2), and adding a specified amount of aqueous solution containing a substance that is easily decomposed by aerobic microorganisms to the mixed liquid in the aeration tank and measuring changes in DO in the process of aeration of the mixed liquid (step 3). This inspection set is repeated, and a change curve of DO or characteristic values characterizing the change curve in each step are acquired by processing the measurement results with a computer to evaluate the aptitude of treatment on the above-mentioned sample waste liquid. However, this inspection method requires complex operations, and automation of all the operations requires a complex and expensive inspection device. As described above, the quality and amount of untreated water, the mesh size of a screen, the capacity of the aeration tank, the capacity of a precipitation tank, and the like differ from one wastewater treatment facility to another, and BOD values, soluble SS values, refractory SS values, and the like therefore vary. There are no values proper in all worksites, and a dissolved oxygen concentration at which the activated sludge is stable is a proper value in that worksite at that water temperature, with that load, and in that environment. In other words, what is required is not such management as to fit the microorganism balance in the activated sludge to a fixed proper dissolved oxygen content but is adjustment to the proper dissolved oxygen content according to the activated sludge. However, a measurement method for obtaining an index for determining whether a dissolved oxygen content in an aeration tank is appropriate has not been conventionally known. Also, a measurement method that enables an appropriate grasp of the state of an aeration tank in relation to the activated sludge has not been known in terms of not only the dissolved oxygen content but also other elements, and development of such a measurement method has been desired.

SUMMARY OF THE INVENTION

Object to be Solved by the Invention

An object of the present invention is to solve the above problems and to provide an index for determining whether a dissolved oxygen content in an aeration tank in a wastewater treatment facility is appropriate. Another object is to provide a testing method and a testing apparatus for obtaining the index, and a diagnosis method and an operation management method of a wastewater treatment facility using the index.

Means to Solve the Object

Biological treatment using microorganisms is the core of a wastewater treatment facility, but activated sludge used in the wastewater treatment facility contains many microorganisms of various types. Hence, it is difficult to theoretically elucidate changes in the activated sludge, which is a mass of microorganisms, and the environment around each wastewater treatment facility, such as the type of and amount of an inflow load, the state of activated sludge, and a climate such as the air temperature and humidity, differ from one treatment facility to another. These facts are major reasons why a method of appropriately maintaining the operation of a wastewater treatment facility has not been developed. In such a situation, a measurement method that enables an appropriate grasp of the state of an aeration tank in relation to the activated sludge has not been developed. The present inventors have examined and observed many wastewater treatment facilities of many types and have found on the basis of the resulting findings a simple measurement method that enables an appropriate grasp of the state of an aeration tank in relation to activated sludge. This method utilizes a conventional method for measuring SV30, in which two 1-L graduated cylinders are provided, an activated sludge mixed liquid and water containing more oxygen than the activated sludge mixed liquid are added to one of the cylinders to provide a solution containing much oxygen, the activated sludge mixed liquid and deoxidized water are added to the other cylinder to provide a solution containing less oxygen than the activated sludge mixed liquid, both containers are left standing, and the volume ratios of precipitates are measured after 30 minutes in substantially the same manner as in measurements of SV30. It has been found not only that the difference between measured values of both containers reveals whether the dissolved oxygen content in the aeration tank at that time is proper for the activated sludge content but also that information about whether the amount of load is appropriate for the activated sludge content and about abnormal conditions of the activated sludge is obtained. The present invention has thus been completed.

More specifically, the present invention is specified by the following items.

(1) A testing method for testing a state of an aeration tank in a wastewater treatment facility, comprising obtaining a difference between: a sedimentation amount when a given period of time has elapsed after an activated sludge mixed liquid collected from the aeration tank and water having a higher dissolved oxygen concentration than the activated sludge mixed liquid are poured into the same container and mixed together; and a sedimentation amount when a period of time equal to the given period of time has elapsed after the activated sludge mixed liquid collected from the aeration tank and water having a lower dissolved oxygen concentration than the activated sludge mixed liquid are poured into the same container and mixed together.

(2) The testing method according to item (1) above, wherein a volume ratio between the activated sludge mixed liquid and the water having a higher dissolved oxygen concentration than the activated sludge mixed liquid is 3:7 to 4:6, and wherein a volume ratio between the activated sludge mixed liquid and the water having a lower dissolved oxygen concentration than the activated sludge mixed liquid is 3:7 to 4:6.

(3) The testing method according to item (1) or (2) above, wherein a dissolved oxygen content in the water having a higher dissolved oxygen concentration than the activated sludge mixed liquid is 7.5 to 10.0 mg/L, and wherein a dissolved oxygen content in the water having a lower dissolved oxygen concentration than the activated sludge mixed liquid is 0.0 to 3.5 mg/L.

(4) The testing method according to any one of items (1) to (3) above, wherein the given period of time is 30 minutes.

(5) A method for diagnosing a state of an aeration tank, comprising: collecting an activated sludge mixed liquid from an aeration tank of a wastewater treatment facility; performing a test by the testing method according to any one of claims 1 to 4 using the collected activated sludge mixed liquid; and determining whether a dissolved oxygen content in the aeration tank is appropriate based on a result obtained.

(6) A method for managing operation of a wastewater treatment facility, comprising: collecting an activated sludge mixed liquid from an aeration tank of a wastewater treatment facility; performing a test by the testing method according to any one of claims 1 to 4 using the collected activated sludge mixed liquid; and maintaining, increasing, or decreasing an oxygen content based on a result obtained.

(7) An apparatus for testing a state of an aeration tank of a wastewater treatment facility, comprising at least one selected from: an automatic sampling device for collecting an activated sludge mixed liquid from the aeration tank; an automatic injecting device for injecting the sampled activated sludge mixed liquid and water having a higher dissolved oxygen concentration than the activated sludge mixed liquid or water having a lower dissolved oxygen concentration than the activated sludge mixed liquid into a test container; a mixing device for mixing the injected activated sludge mixed liquid and the water having a higher dissolved oxygen concentration than the activated sludge mixed liquid or the water having a lower dissolved oxygen concentration than the activated sludge mixed liquid; a timer for setting a still-standing time of the test container; an automatic measuring device of the sedimented sludge interface; an automatic discharging device of the mixed liquid in the test container; an automatic cleaning device of the test container; and an automatic display device of a measurement result.

BRIEF DESCRIPTION OF DRAWINGS

FIG. 1 schematically shows a testing method of the present invention.

DETAILED DESCRIPTION OF THE INVENTION

By the testing method of the present invention, information serving as an index for determining whether the dissolved oxygen content in the aeration tank is proper in relation to the activated sludge content is obtained. By the testing method of the present invention, information serving as an index for determining whether the amount of load is proper in relation to the activated sludge content and information about abnormal conditions of the activated sludge can be obtained. By the diagnosis method of the present invention, whether the dissolved oxygen content in the aeration tank is appropriate, whether the amount of load is appropriate, and the state of the aeration tank, such as abnormal conditions of the activated sludge, can be determined using the results obtained by the testing method of the present invention. By the operation management method of the present invention, the oxygen content and the amount of load can be appropriately kept, increased, or decreased using the results obtained by the testing method of the present invention. The testing apparatus of the present invention can efficiently implement the testing method of the present invention.

Mode of Carrying Out the Invention

A testing method for testing a state of an aeration tank in a wastewater treatment facility of the present invention comprises obtaining a difference between: a sedimentation amount when a given period of time has elapsed after an activated sludge mixed liquid collected from the aeration tank and water having a higher dissolved oxygen concentration than the activated sludge mixed liquid are poured into the same container and mixed together; and a sedimentation amount when a period of time equal to the given period of time has elapsed after the activated sludge mixed liquid collected from the aeration tank and water having a lower dissolved oxygen concentration than the activated sludge mixed liquid are poured into the same container and mixed together. For example, the testing method of the present invention can be implemented by providing two containers, adding to one of the containers (container A) and mixing an activated sludge mixed liquid collected from an aeration tank and water having a higher dissolved oxygen concentration than the activated sludge mixed liquid, adding to the other container (container B) and mixing the activated sludge mixed liquid collected from the same aeration tank and water having a lower dissolved oxygen concentration than the activated sludge mixed liquid, leaving both containers standing, and obtaining a difference between the sedimentation amount in the container A and the sedimentation amount in the container B after a given period of time has elapsed. The containers used in the present invention can accommodate the activated sludge mixed liquid, the water having a higher dissolved oxygen concentration than the activated sludge mixed liquid, and the water having a lower dissolved oxygen concentration than the activated sludge mixed liquid and are not limited to particular containers as long as the containers are transparent or semitransparent to such a degree that the interface between the precipitate and the supernatant liquid can be seen. Use of 1-L graduated cylinders used for measurements of the activated sludge volume (SV30) defined by JIS is preferable. The testing method of the present invention is preferably implemented using an activated sludge mixed liquid collected from the final aeration tank or an activated sludge mixed liquid collected in the final step of the aeration tank operation in the case of the batch aeration sedimentation method. The activated sludge mixed liquid refers to the mixed liquid of the treated liquid and the sludge in the aeration tank.

The water having a higher dissolved oxygen concentration than the activated sludge mixed liquid (hereinafter also referred to as "oxygen-dissolved water") in the present invention has a dissolved oxygen concentration higher than the dissolved oxygen concentration of the activated sludge mixed liquid and is not limited to particular water as long as the water does not contain substances that affect formation of a precipitate other than dissolved oxygen, and components contained in ordinary water such as tap water may be contained. Tap water commonly contains 7 to 8 mg/L of oxygen dissolved, and examples of suitable oxygen-dissolved water include tap water. The examples also include industrial water, groundwater, and reclaimed water having a high dissolved oxygen concentration, and an aqueous solution that does not have much effect on the testing method of the present invention compared with the case where water is used can also be used. The dissolved oxygen content in the oxygen-dissolved water is preferably 7.5 to 10.0 mg/L, more preferably 8.0 to 9.0 mg/L. The water having a lower dissolved oxygen concentration than the activated sludge mixed liquid (hereinafter also referred to as "deoxidized water") in the present invention has a dissolved oxygen concentration lower than the dissolved oxygen concentration of the activated sludge mixed liquid and is not limited to particular water as long as the water does not contain substances that affect formation of a precipitate other than dissolved oxygen, and components contained in ordinary water such as tap water may be contained. Examples of the deoxidized water include water obtained by removing oxygen from ordinary water such as tap water by adding a chemical such as an oxygen scavenger or degassing or boiling treatment such ordinary water. An aqueous solution that does not have much effect on the testing method of the present invention compared with the case where water is used can also be used. In the case where deoxidized water prepared by boiling treatment is used, the water is allowed to have a water temperature equal to that of water used as the oxygen-dissolved water. Untreated water in an untreated water tank or an equalization tank without aeration having a sufficiently low dissolved oxygen concentration as a result of consumption of oxygen by microorganisms can also be used as long as the SS concentration, which affects test results of the present invention, is sufficiently low. The dissolved oxygen content in the deoxidized water is preferably 0.0 to 3.5 mg/L, more preferably 0.0 to 1.5 mg/L. The mixing treatment of the activated sludge mixed liquid and the oxygen-dissolved water and the mixing treatment of the activated sludge mixed liquid and the deoxidized water are not limited to particular treatments, and a known method can be used as appropriate. Examples of the method include generating vibrations by shaking the container, turning the container upside down, and stirring using a stirrer put into the container. The measurement of the sedimentation amount in the testing method of the present invention is preferably performed in terms of volume by visually reading the interface of the sedimented sludge as in conventional sludge volume tests (SV tests) after standing still for a given period of time. The sedimentation amount is preferably represented by the ratio of the volume of the precipitate to the total volume of the activated sludge mixed liquid and the oxygen-dissolved water and the ratio of the volume of the precipitate to the total volume of the activated sludge mixed liquid and the deoxidized water as in conventional SV tests. By the testing method of the present invention, the state of the aeration tank, such as whether the oxygen content is proper, can be determined on the basis of the difference between these sedimentation amounts.

The amounts and mixing ratio of the activated sludge mixed liquid, the oxygen-dissolved water, and the deoxidized water are not limited to particular values. The total amount of the activated sludge mixed liquid and the oxygen-dissolved water is preferably equal to the total amount of the activated sludge mixed liquid and the deoxidized water, and the ratio between the activated sludge mixed liquid and the oxygen-dissolved water is preferably equal to the ratio between the activated sludge mixed liquid and the deoxidized water. The ratio between the activated sludge mixed liquid and the oxygen-dissolved water and the ratio between the activated sludge mixed liquid and the deoxidized water are not limited to particular ratios. For example, the amount of the oxygen-dissolved water or the deoxidized water can fall within the range of 2 to 8 times, 1.3 to 5 times, or 1.5 to 3.5 times the amount of the activated sludge mixed liquid in terms of volume. The ratio between the activated sludge mixed liquid and the oxygen-dissolved water and the ratio between the activated sludge mixed liquid and the deoxidized water are both preferably 3:7 to 4:6 in terms of volume. The total amount of the activated sludge mixed liquid and the oxygen-dissolved water and the total amount of the activated sludge mixed liquid and the deoxidized water are preferably 1 L because a conventional SV meter can be used. The testing method of the present invention can be implemented by measuring two sedimentation amounts at the same time using separate containers as described above or by measuring one sedimentation amount before the other sedimentation amount is measured using one container. The situation of operation management in the final aeration tank can be determined by comparison because the situation does not greatly fluctuate during a short time of about 30 minutes required for the measurement in the testing method of the present invention unless operation management such as the oxygen content and the return sludge is not changed during a short time between first sampling and second sampling of the mixed liquid in the final aeration tank.

Figure 1A:
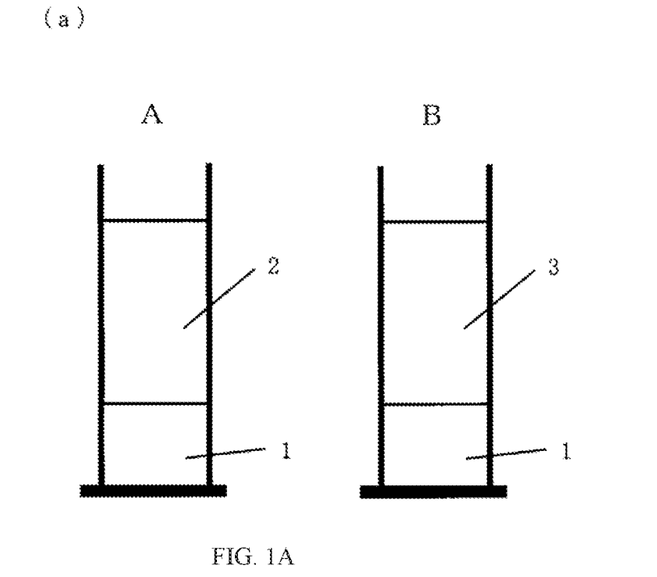
FIG. 1(a) shows injection of an activated sludge mixed liquid and oxygen-dissolved water or deoxidized water into containers.
Figure 1B:
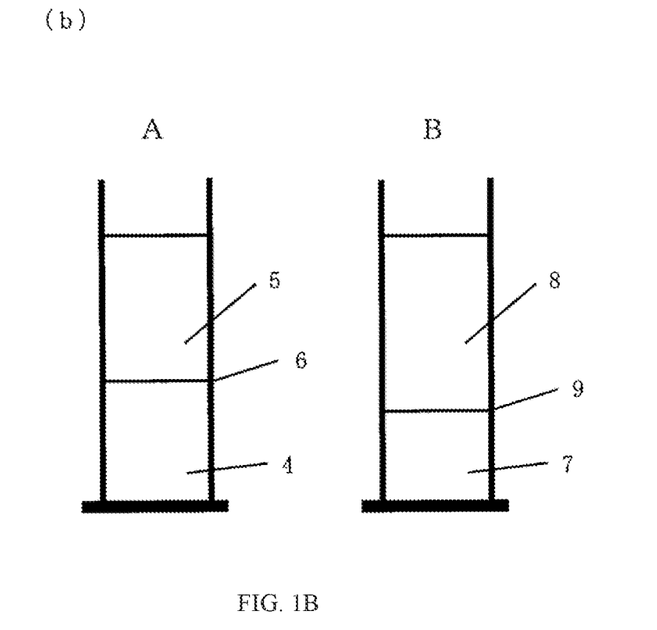
FIG. 1(b) shows the state after the activated sludge mixed liquid and the oxygen-dissolved water or the deoxidized water are mixed together and left standing for a given period of time.

An embodiment of the testing method of the present invention is further described. The testing method of the present invention is also referred to as an SV comparative difference testing method. For example, in the case where 1-L graduated cylinders are used as the containers A and B, 300 mL of the activated sludge mixed liquid and 700 mL of the oxygen-dissolved water are poured to the container A to reach a total amount of 1 L (1,000 mL). Also, 300 mL of the activated sludge mixed liquid and 700 mL of the deoxidized water are poured to the container B to reach a total amount of 1 L (1,000 mL). Both containers containing sample prepared in this way are left standing. After a given period of time has elapsed, the volume of the precipitate in the container A and the volume of the precipitate in the container B are measured by visually reading the interfaces of the sedimented sludge. The volume ratio of the precipitate in each container is represented on a percentage basis, and the difference between both values is determined. For example, in the case where the samples in both containers are prepared as described above using 1-L graduated cylinders as the containers, the volume ratio of the precipitate in the container A is 35% (350/1,000×100) when the volume of the precipitate is 350 mL, and the volume ratio of the precipitate in the container B is 30% (300/1,000×100) when the volume of the precipitate is 300 mL, so that the difference is 5%. The given period of time can be appropriately determined to observe changes in the amount of the precipitate. Examples of the given period of time include ranges of 3 minutes to 24 hours, 3 minutes to 5 hours, 3 minutes to 3 hours, and 10 minutes to 30 minutes, and 30 minutes, 60 minutes, 120 minutes, or 24 hours can be employed. The given period of time is preferably 30 minutes. Determination of the interface between the precipitate and the supernatant liquid, that is, determination of the volume of the precipitate, can be performed in substantially the same way as in the case of the measurement of the sludge volume (SV30) defined by JIS. FIG. 1 schematically shows a measurement method of the present invention. FIG. 1(a) shows preparation of measurement samples. An activated sludge mixed liquid 1 and oxygen-dissolved water 2 are charged into the container A at a volume ratio of 3:7. The activated sludge mixed liquid 1 and deoxidized water 3 are charged into the container B at a volume ratio of 3:7. FIG. 2(b) shows the state of the container A when the given period of time has elapsed after the activated sludge mixed liquid 1 and the oxygen-dissolved water 2 in the container A are mixed together and the state of the container B when the given period of time has elapsed after the activated sludge mixed liquid 1 and the deoxidized water 3 in the container B are mixed together. In the container A, a precipitate 4 precipitated has a volume determined by an interface 6 with supernatant liquid 5, and the volume ratio of the precipitate 4 is represented by the volume of the precipitate 4/(the volume of the precipitate 4+the volume of the supernatant liquid 5). In the container B, a precipitate 7 precipitated has a volume determined by an interface 9 with supernatant liquid 8, and the volume ratio of the precipitate 6 is represented by the volume of the precipitate 6/(the volume of the precipitate 6+the volume of the supernatant liquid 7). The difference is then determined.

In the testing method of the present invention, the difference between the result (hereinafter referred to as a "water SV value") obtained using oxygen-containing water and the result (hereinafter referred to as a "deoxidized SV value") obtained using deoxidized water indicates the following states. In the case where the activated sludge mixed liquid in the final aeration tank is measured by the testing method of the present invention, the load must be digested when the activated sludge is in a proper state. Accordingly, in the measurement of the water SV value in a state where oxygen is oversupplied to the activated sludge, the activated sludge bulks to some extent. On the other hand, the deoxidized SV value indicates ordinary sedimentation. Hence, the water SV value is a little higher than the deoxidized SV value. In this case, a proper oxygen state (proper dissolved oxygen state) has been achieved, and adjustment of a blower is not required. In the case where the water SV value is higher than the deoxidized SV value and where the difference is large, the state indicated is a state where oxygen is further supplied to the bulking activated sludge and where oxygen is excessive in the activated sludge. In this case, the blower is required to be adjusted to reduce the air volume. As described above, by the testing method of the present invention, whether the dissolved oxygen content in the aeration tank is proper can be determined on the basis of the results. A deoxidized SV value higher than the water SV value indicates that the water SV value is low, and the activated sludge is in such a state where sedimentation is improved by supplying oxygen. This situation indicates that the activated sludge is not fully digesting the inflow load, that is, an overloaded state. As described above, by the testing method of the present invention, whether the amount of load is proper for the microorganisms can be determined on the basis of the results. There is a case where the activated sludge bulks such that filamentous bacteria are emphasized like cotton candy in the container for measurement of the water SV value and where string-like bacteria are emphasized in the activated sludge in the container for measurement of the deoxidized SV value. In this case, by the testing method of the present invention, the fact that filamentous bacteria are dominant can be found in 30 minutes without observation for a long time.

A method for diagnosing a state of an aeration tank of the present invention comprises collecting an activated sludge mixed liquid from an aeration tank of a wastewater treatment facility, performing a test by the testing method of the present invention using the collected activated sludge mixed liquid, and determining whether the dissolved oxygen content in the aeration tank is appropriate based on a result obtained. Whether the dissolved oxygen content is appropriate can be determined as described in paragraph 0017 above. When the water SV value is compared with the deoxidized SV value, the oxygen content can be determined to be appropriate if the water SV value is about 1.03 to 1.05 times as high as the deoxidized SV value, the oxygen content can be determined to be excessive compared with an optimal oxygen content if the water SV value is higher than 1.03 to 1.05 times of the deoxidized SV value, leading to the trend that the sludge floc further bulks if the present oxygen content is kept, and the oxygen content can be determined to be lacking compared with the optimal oxygen content if the water SV value is lower than 1.03 to 1.05 times of the deoxidized SV value, in which the remaining water pollutants can be further absorbed, digested, and decomposed by increasing the oxygen content. In addition, by the method for diagnosing a wastewater treatment facility of the present invention, whether the amount of load is appropriate can be determined, and abnormal conditions of the activated sludge can be found. A method for managing operation of a wastewater treatment facility of the present invention comprises collecting an activated sludge mixed liquid from an aeration tank of a wastewater treatment facility, performing a test by the testing method of the present invention using the collected activated sludge mixed liquid, and maintaining, increasing, or decreasing an oxygen content based on a result obtained. Since whether the dissolved oxygen content is appropriate can be determined on the basis of the results obtained by the testing method of the present invention, stable operation of the wastewater treatment facility can be achieved by keeping the oxygen content in the case where the dissolved oxygen content is proper, increasing the oxygen content in the case where the dissolved oxygen content is lacking, and reducing the oxygen content in the case where the dissolved oxygen content is excessive. Since the testing method of the present invention enables decision of whether the amount of load is appropriate and discovery of abnormal conditions of the activated sludge in addition to decision of whether the dissolved oxygen content is appropriate, by the operation management method of the present invention, stable operation of the wastewater treatment facility can be achieved by keeping the inflow of the load when the amount of load is proper, increasing the inflow of the load when the amount of load is lacking, and reducing the inflow of the load when the amount of load is excessive (overloaded). Since the trend that the filamentous bacteria become dominant can be found at an early stage by the measurement method of the present invention, in the case where the trend that the filamentous bacteria are dominant is found, generation of filamentous bacteria can be inhibited by charging a germicide for filamentous bacteria by the operation management method of the present invention. The aeration method is not limited to a standard method of blowing air with a blower through a diffuser tube provided at the bottom of the aeration tank but may be any method such as the surface aeration method and a method of blowing oxygen instead of air. For operation management of a large-scale wastewater treatment equipment, an automatic SV measuring device of the interface measurement type utilizing transmitted light is available on the market, and such an automatic SV measuring device can also be used for the testing method of the present invention. Combining an automatic diluter or the like with the device enables display of values obtained from the test results of the present invention and the results of decision based on the results or output of the results as signals for operation management of the aeration tank.

A testing apparatus of the present invention is configured to test a state of an aeration tank of a wastewater treatment facility and comprises at least one selected from an automatic sampling device for collecting an activated sludge mixed liquid from the aeration tank, an automatic injecting device for injecting the sampled activated sludge mixed liquid and water having a higher dissolved oxygen concentration than the activated sludge mixed liquid or water having a lower dissolved oxygen concentration than the activated sludge mixed liquid into a test container, a mixing device for mixing the injected activated sludge mixed liquid and the water having a higher dissolved oxygen concentration than the activated sludge mixed liquid or the water having a lower dissolved oxygen concentration than the activated sludge mixed liquid, a timer for setting a still-standing time of the test container, an automatic measuring device of the sedimented sludge interface, an automatic discharging device of the mixed liquid in the test container, an automatic cleaning device of the test container, and an automatic display device of a measurement result. The testing apparatus of the present invention can efficiently implement the testing method of the present invention because the device comprises these constituents. The automatic sampling device in the testing apparatus of the present invention can utilize a known method of performing automatic sampling from a container accommodating a solution or a dispersion. For example, a mechanism that automatically implements a method such as suction using a suction pipe for sucking the activated sludge mixed liquid inserted into the aeration tank and provision, for the aeration tank, of an outlet for extracting the activated sludge mixed liquid out of the aeration tank can be employed. For the automatic injecting device, a known method of automatically injecting a liquid into a container can be used. For example, a mechanism that automatically implements a method of inserting injection pipes respectively communicating with a tank containing the sampled activated sludge mixed liquid, a tank containing the oxygen-dissolved water, or a tank containing the deoxidized water into a test container to inject the respective liquids into the test container can be employed. For the mixing device and the timer, known methods and devices can be employed as appropriate. Examples of the mixing device include a shaking device that vibrates the test container, a reversing device that turns a lidded test container upside down, and a stirrer. For the automatic measuring device of the sedimented sludge interface, a known method of recognizing the position of the interface between the precipitate and the liquid can be used, and for example, a device utilizing light such as transmitted light can be used. Known methods and devices can be used for the automatic discharging device, the automatic cleaning device, and the automatic display device. Examples of the automatic discharging device include a method and a reversing device for turning the test container upside down, examples of the automatic cleaning device include a method and device for injecting a cleaner into the container and brushing the container, and examples of the automatic display device include a display employing a liquid crystal.

The state of the activated sludge can be determined well by the testing method of the present invention alone as described above, but the state of the activated sludge can be more accurately determined by combination with another method. Examples of another testing method that can be combined include SV30, SV24-hours, pH, ORP, sludge ORP, OD, transparency, and visual SV observation. These testing methods are commonly used in wastewater treatment facilities using activated sludge and can be implemented in an ordinary manner. For example, in the case where the SV comparative difference testing method is combined with ORP and/or OD, when more than a proper amount of oxygen is supplied for the load, that is, when more than an ordinary amount of load inflows in relation to an ordinary activated sludge content and more than an ordinary oxygen content is supplied, the concentrations of both ORP and OD are high, and the supply of oxygen tends to be determined to be sufficient. However, the SV comparative difference testing method shows the situation where the water SV value is lower than the deoxidized SV value and where oxygen is lacking for the activated sludge. Hence, the overloaded state continues unless the activated sludge content is increased if the amount of load is supplied as it is, and it is shown that the amount of oxygen supplied must be kept as it is without reducing the amount of oxygen supplied. In the case where the SV comparative difference testing method and pH are used, for example, in the case of the treatment of wastewater predominantly containing a system containing a lot of nitrogen components, the pH decreases to neutral or acidic as the purification progresses. When the pH is in this state, this state tends to be allowed to continue because the treatment of the load is progressing, but the pH may be alkaline due to breakup of the activated sludge if this treatment (supply of oxygen) progresses. Also in this case, bulking in the oxygen-dissolved water side is greater than in the deoxidized water side in the SV comparative difference testing method, and the proper amount of oxygen is not misestimated. With the combination of the SV comparative difference testing method and visual observation, if filamentous bacteria exist in the oxygen-dissolved water side, the sludge more greatly bulks than in the case of SV30-minutes to show a bulking form like cotton candy. If filamentous bacteria exist in the deoxidized water side, lines tend to be more quickly and clearly observed in the sedimented sludge than in the case of SV30-minutes. It is found that the longer and thicker the lines, the further the rate of priority of the filamentous bacteria is increased.

EXAMPLES

Example 1

Two 1-L graduated cylinders were provided, and an activated sludge mixed liquid was collected from a final aeration tank of a wastewater treatment facility. Into each graduated cylinder, 300 mL of the activated sludge mixed liquid was charged. To one of the graduated cylinders, 700 mL of tap water was added, and 700 mL of cooled boiled water (deoxidized water) was added to the other graduated cylinder. A set of operations including lidding the graduated cylinders, turning the graduated cylinders upside down, and restoring the posture was repeated several times to mix the liquids in the graduated cylinders, and the graduated cylinders were left standing. After 30 minutes had elapsed after standing, the sedimentation amount was measured by visually observing the sedimented sludge interface in each graduated cylinder, and the volume ratio of the precipitate was calculated. The sedimentation amount was larger in the case of tap water, and the difference from the case of cooled boiled water was 3%. Since the measured values indicated that the oxygen content is proper, the oxygen content at that time was kept without adjusting a blower, so that a stable operation state continued.

Example 2

An activated sludge mixed liquid was collected from the final aeration tank of the wastewater treatment facility, and measurements were performed in substantially the same manner as in Example 1. The measured value was higher in the case of tap water, and the difference from the case of cooled boiled water was 10%. Since the measured values indicated that oxygen is excessive, the oxygen content was reduced by adjusting the blower, so that the interface in a precipitation tank was lowered to stabilize the operation state.

Example 3

An activated sludge mixed liquid was collected from the final aeration tank of the wastewater treatment facility, and measurements were performed in substantially the same manner as in Example 1. The measured value was higher in the case of cooled boiled water, and the difference from the case of tap water was 10%. Since the measured values indicated an overloaded state, the oxygen content was increased, so that the treated water transparency was improved to stabilize the operation state was stabilized.

Example 4

An activated sludge mixed liquid was collected from the final aeration tank of the wastewater treatment facility, and measurements were performed in substantially the same manner as in Example 1. Filamentous bacteria generated like cotton candy in the case of tap water, and string-like lines were observed in the case of cooled boiled water. A counteragent against filamentous bacteria was charged to the aeration tank on the basis of this result, so that generation of the filamentous bacteria was inhibited.

INDUSTRIAL APPLICABILITY

The testing method, diagnosis method, and operation management method of the present invention can be suitably applied to various wastewater treatment facilities and enable an appropriate grasp of the state of the aeration tank in relation to the activated sludge, so that appropriate diagnosis of the state of health of the activated sludge and appropriate operation management can be performed.

Explanation of Letters or Numerals 1 activated sludge mixed liquid
2 oxygen-dissolved water
3 deoxidized water
4 precipitate
5 supernatant liquid
6 interface
7 precipitate
8 supernatant liquid
9 interface

REFERENCES

Patent Documents

Patent Document 1: Japanese unexamined Patent Application Publication No. 6-126293
Patent Document 2: Japanese unexamined Patent Application Publication No. 11-90480
Patent Document 3: Japanese unexamined Patent Application Publication No. 11-160305

What is claimed is:

1. A testing method for testing a state of an aeration tank in a wastewater treatment facility, comprising obtaining a difference between: a sedimentation amount when a given period of time has elapsed after an activated sludge mixed liquid collected from the aeration tank and water having a higher dissolved oxygen concentration than the activated sludge mixed liquid are poured into the same container and mixed together; and a sedimentation amount when a period of time equal to the given period of time has elapsed after the activated sludge mixed liquid collected from the aeration tank and water having a lower dissolved oxygen concentration than the activated sludge mixed liquid are poured into the same container and mixed together.

2. The testing method according to claim 1, wherein:
a first volume ratio between the activated sludge mixed liquid and the water having a higher dissolved oxygen concentration than the activated sludge mixed liquid is 3:7 to 4:6; and
a second volume ratio between the activated sludge mixed liquid and the water having a lower dissolved oxygen concentration than the activated sludge mixed liquid is 3:7 to 4:6.

3. The testing method according to claim 1, wherein:
a first dissolved oxygen content in the water having a higher dissolved oxygen concentration than the activated sludge mixed liquid is 7.5 to 10.0 mg/L; and
a second dissolved oxygen content in the water having a lower dissolved oxygen concentration than the activated sludge mixed liquid is 0.0 to 3.5 mg/L.

4. The testing method according to claim 1, wherein the given period of time is 30 minutes.

5. A method for diagnosing a state of an aeration tank, comprising:
collecting the activated sludge mixed liquid from the aeration tank of the wastewater treatment facility;
performing the test by the testing method according to claim 1 using the collected activated sludge mixed liquid; and
determining whether a dissolved oxygen content in the aeration tank is appropriate based on the difference of sedimentation amounts,
wherein the difference of sedimentation amounts is obtained as a difference between a ratio of a volume of a precipitate (a water SV value) to a total volume of the activated sludge mixed liquid and the water having the higher dissolved oxygen concentration than the activated sludge mixed liquid, and a ratio of a volume of a precipitate (a deoxidized SV value) to the total volume of the activated sludge mixed liquid and the water having the lower dissolved oxygen concentration than the activated sludge mixed liquid,
wherein the dissolved oxygen content in the aeration tank is appropriate if the water SV value is 1.03 to 1.05 times of the deoxidized SV value,
wherein the dissolved oxygen content in the aeration tank is excessive compared with an optimal dissolved oxygen content if the water SV value is higher than 1.05 times of the deoxidized SV value, and
wherein the dissolved oxygen content in the aeration tank is lacking compared with the optimal dissolved oxygen content if the water SV value is lower than 1.03 times of the deoxidized SV value.

6. A method for managing operation of a wastewater treatment facility, comprising:
collecting the activated sludge mixed liquid from the aeration tank of the wastewater treatment facility;
performing the test by the testing method according to claim 1 using the collected activated sludge mixed liquid; and
maintaining, increasing, or decreasing a dissolved oxygen content in the aeration tank based on the difference of sedimentation amounts,
wherein the difference of sedimentation amounts is obtained as a difference between a ratio of a volume of a precipitate (a water SV value) to a total volume of the activated sludge mixed liquid and the water having the higher dissolved oxygen concentration than the activated sludge mixed liquid, and a ratio of a volume of a precipitate (a deoxidized SV value) to the total volume of the activated sludge mixed liquid and the water having the lower dissolved oxygen concentration than the activated sludge mixed liquid, wherein the dissolved oxygen content in the aeration tank is maintained if the water SV value is 1.03 to 1.05 times of the deoxidized SV value, wherein the dissolved oxygen content in the aeration tank is increased if the water SV value is lower than 1.03 times of the deoxidized SV value, and wherein the dissolved oxygen content in the aeration tank is decreased if the water SV value is higher than 1.05 times of the deoxidized SV value.

7. The testing method according to claim 2, wherein:
a first dissolved oxygen content in the water having a higher dissolved oxygen concentration than the activated sludge mixed liquid is 7.5 to 10.0 mg/L; and
a second dissolved oxygen content in the water having a lower dissolved oxygen concentration than the activated sludge mixed liquid is 0.0 to 3.5 mg/L.

8. The testing method according to claim 2, wherein the given period of time is 30 minutes.

9. The testing method according to claim 3, wherein the given period of time is 30 minutes.

10. The testing method according to claim 7, wherein the given period of time is 30 minutes.

11. A method for diagnosing a state of an aeration tank, comprising:
collecting the activated sludge mixed liquid from the aeration tank of the wastewater treatment facility;
performing the test by the testing method according to claim 2 using the collected activated sludge mixed liquid; and
determining whether a dissolved oxygen content in the aeration tank is appropriate based on the difference of sedimentation amounts,
wherein the difference of sedimentation amounts is obtained as a difference between a ratio of a volume of a precipitate (a water SV value) to a total volume of the activated sludge mixed liquid and the water having the higher dissolved oxygen concentration than the activated sludge mixed liquid, and a ratio of a volume of a precipitate (a deoxidized SV value) to the total volume of the activated sludge mixed liquid and the water having the lower dissolved oxygen concentration than the activated sludge mixed liquid,
wherein the dissolved oxygen content in the aeration tank is appropriate if the water SV value is 1.03 to 1.05 times of the deoxidized SV value,
wherein the dissolved oxygen content in the aeration tank is excessive compared with an optimal dissolved oxygen content if the water SV value is higher than 1.05 times of the deoxidized SV value, and
wherein the dissolved oxygen content in the aeration tank is lacking compared with the optimal dissolved oxygen content if the water SV value is lower than 1.03 times of the deoxidized SV value.

12. A method for diagnosing a state of an aeration tank, comprising:
collecting the activated sludge mixed liquid from the aeration tank of the wastewater treatment facility;
performing the test by the testing method according to claim 3 using the collected activated sludge mixed liquid; and
determining whether a dissolved oxygen content in the aeration tank is appropriate based on the difference of sedimentation amounts,
wherein the difference of sedimentation amounts is obtained as a difference between a ratio of a volume of a precipitate (a water SV value) to a total volume of the activated sludge mixed liquid and the water having the higher dissolved oxygen concentration than the activated sludge mixed liquid, and a ratio of a volume of a precipitate (a deoxidized SV value) to the total volume of the activated sludge mixed liquid and the water having the lower dissolved oxygen concentration than the activated sludge mixed liquid,
wherein the dissolved oxygen content in the aeration tank is appropriate if the water SV value is 1.03 to 1.05 times of the deoxidized SV value,
wherein the dissolved oxygen content in the aeration tank is excessive compared with an optimal dissolved oxygen content if the water SV value is higher than 1.05 times of the deoxidized SV value, and
wherein the dissolved oxygen content in the aeration tank is lacking compared with the optimal dissolved oxygen content if the water SV value is lower than 1.03 times of the deoxidized SV value.

13. A method for diagnosing a state of an aeration tank, comprising:
collecting the activated sludge mixed liquid from the aeration tank of the wastewater treatment facility;
performing the test by the testing method according to claim 8 using the collected activated sludge mixed liquid; and
determining whether a dissolved oxygen content in the aeration tank is appropriate based on the difference of sedimentation amounts,
wherein the difference of sedimentation amounts is obtained as a difference between a ratio of a volume of a precipitate (a water SV value) to a total volume of the activated sludge mixed liquid and the water having the higher dissolved oxygen concentration than the activated sludge mixed liquid, and a ratio of a volume of a precipitate (a deoxidized SV value) to the total volume of the activated sludge mixed liquid and the water having the lower dissolved oxygen concentration than the activated sludge mixed liquid,
wherein the dissolved oxygen content in the aeration tank is appropriate if the water SV value is 1.03 to 1.05 times of the deoxidized SV value,
wherein the dissolved oxygen content in the aeration tank is excessive compared with an optimal dissolved oxygen content if the water SV value is higher than 1.05 times of the deoxidized SV value, and
wherein the dissolved oxygen content in the aeration tank is lacking compared with the optimal dissolved oxygen content if the water SV value is lower than 1.03 times of the deoxidized SV value.

14. A method for diagnosing a state of an aeration tank, comprising:
collecting the activated sludge mixed liquid from the aeration tank of the wastewater treatment facility;
performing the test by the testing method according to claim 8 using the collected activated sludge mixed liquid; and
determining whether a dissolved oxygen content in the aeration tank is appropriate based on the difference of sedimentation amounts,
wherein the difference of sedimentation amounts is obtained as a difference between a ratio of a volume of a precipitate (a water SV value) to a total volume of the activated sludge mixed liquid and the water having the higher dissolved oxygen concentration than the activated sludge mixed liquid, and a ratio of a volume of a precipitate (a deoxidized SV value) to the total volume of the activated sludge mixed liquid and the water having the lower dissolved oxygen concentration than the activated sludge mixed liquid, wherein the dissolved oxygen content in the aeration tank is appropriate if the water SV value is 1.03 to 1.05 times of the deoxidized SV value, wherein the dissolved oxygen content in the aeration tank is excessive compared with an optimal dissolved oxygen content if the water SV value is higher than 1.05 times of the deoxidized SV value, and wherein the dissolved oxygen content in the aeration tank is lacking compared with the optimal dissolved oxygen content if the water SV value is lower than 1.03 times of the deoxidized SV value.

15. A method for managing operation of a wastewater treatment facility, comprising:

collecting the activated sludge mixed liquid from the aeration tank of the wastewater treatment facility;

performing the test by the testing method according to claim 2 using the collected activated sludge mixed liquid; and maintaining, increasing, or decreasing a dissolved oxygen content in the aeration tank based on the difference of sedimentation amounts, wherein the difference of sedimentation amounts is obtained as a difference between a ratio of a volume of a precipitate (a water SV value) to a total volume of the activated sludge mixed liquid and the water having the higher dissolved oxygen concentration than the activated sludge mixed liquid, and a ratio of a volume of a precipitate (a deoxidized SV value) to the total volume of the activated sludge mixed liquid and the water having the lower dissolved oxygen concentration than the activated sludge mixed liquid, wherein the dissolved oxygen content in the aeration tank is maintained if the water SV value is 1.03 to 1.05 times of the deoxidized SV value, wherein the dissolved oxygen content in the aeration tank is increased if the water SV value is lower than 1.03 times of the deoxidized SV value, and wherein the dissolved oxygen content in the aeration tank is decreased if the water SV value is higher than 1.05 times of the deoxidized SV value.

16. A method for managing operation of a wastewater treatment facility, comprising:

collecting the activated sludge mixed liquid from the aeration tank of the wastewater treatment facility;

performing the test by the testing method according to claim 3 using the collected activated sludge mixed liquid; and maintaining, increasing, or decreasing a dissolved oxygen content in the aeration tank based on the difference of sedimentation amounts, wherein the difference of sedimentation amounts is obtained as a difference between a ratio of a volume of a precipitate (a water SV value) to a total volume of the activated sludge mixed liquid and the water having the higher dissolved oxygen concentration than the activated sludge mixed liquid, and a ratio of a volume of a precipitate (a deoxidized SV value) to the total volume of the activated sludge mixed liquid and the water having the lower dissolved oxygen concentration than the activated sludge mixed liquid, wherein the dissolved oxygen content in the aeration tank is maintained if the water SV value is 1.03 to 1.05 times of the deoxidized SV value, wherein the dissolved oxygen content in the aeration tank is increased if the water SV value is lower than 1.03 times of the deoxidized SV value, and wherein the dissolved oxygen content in the aeration tank is decreased if the water SV value is higher than 1.05 times of the deoxidized SV value.

17. A method for managing operation of a wastewater treatment facility, comprising:

collecting the activated sludge mixed liquid from the aeration tank of the wastewater treatment facility;

performing the test by the testing method according to claim 7 using the collected activated sludge mixed liquid; and maintaining, increasing, or decreasing a dissolved oxygen content in the aeration tank based on the difference of sedimentation amounts, wherein the difference of sedimentation amounts is obtained as a difference between a ratio of a volume of a precipitate (a water SV value) to a total volume of the activated sludge mixed liquid and the water having the higher dissolved oxygen concentration than the activated sludge mixed liquid, and a ratio of a volume of a precipitate (a deoxidized SV value) to the total volume of the activated sludge mixed liquid and the water having the lower dissolved oxygen concentration than the activated sludge mixed liquid, wherein the dissolved oxygen content in the aeration tank is maintained if the water SV value is 1.03 to 1.05 times of the deoxidized SV value, wherein the dissolved oxygen content in the aeration tank is increased if the water SV value is lower than 1.03 times of the deoxidized SV value, and wherein the dissolved oxygen content in the aeration tank is decreased if the water SV value is higher than 1.05 times of the deoxidized SV value.

18. A method for managing operation of a wastewater treatment facility, comprising:

collecting the activated sludge mixed liquid from the aeration tank of the wastewater treatment facility;

performing the test by the testing method according to claim 8 using the collected activated sludge mixed liquid; and maintaining, increasing, or decreasing a dissolved oxygen content in the aeration tank based on the difference of sedimentation amounts, wherein the difference of sedimentation amounts is obtained as a difference between a ratio of a volume of a precipitate (a water SV value) to a total volume of the activated sludge mixed liquid and the water having the higher dissolved oxygen concentration than the activated sludge mixed liquid, and a ratio of a volume of a precipitate (a deoxidized SV value) to the total volume of the activated sludge mixed liquid and the water having the lower dissolved oxygen concentration than the activated sludge mixed liquid, wherein the dissolved oxygen content in the aeration tank is maintained if the water SV value is 1.03 to 1.05 times of the deoxidized SV value, wherein the dissolved oxygen content in the aeration tank is increased if the water SV value is lower than 1.03 times of the deoxidized SV value, and wherein the dissolved oxygen content in the aeration tank is decreased if the water SV value is higher than 1.05 times of the deoxidized SV value.

\* \* \* \* \*